(12) United States Patent
Deng et al.

(10) Patent No.: US 11,786,137 B2
(45) Date of Patent: *Oct. 17, 2023

(54) PHYSIOLOGICAL SAMPLING DURING PREDETERMINED ACTIVITIES

(71) Applicant: Apple Inc., Cupertino, CA (US)

(72) Inventors: Siyi Deng, San Jose, CA (US); Stephen J. Waydo, Saratoga, CA (US); Jay Blahnik, Venice, CA (US); Lun Dong, Cupertino, CA (US); Ian R. Shapiro, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/521,377

(22) Filed: Nov. 8, 2021

(65) Prior Publication Data

US 2022/0054030 A1 Feb. 24, 2022

Related U.S. Application Data

(63) Continuation of application No. 15/991,798, filed on May 29, 2018, now Pat. No. 11,166,640.
(Continued)

(51) Int. Cl.
*A61B 5/024* (2006.01)
*A61B 5/00* (2006.01)
(Continued)

(52) U.S. Cl.
CPC .......... *A61B 5/02405* (2013.01); *A61B 5/021* (2013.01); *A61B 5/0205* (2013.01);
(Continued)

(58) Field of Classification Search
CPC ... A61B 5/02405; A61B 5/0205; A61B 5/021; A61B 5/02416; A61B 5/02427;
(Continued)

(56) References Cited

U.S. PATENT DOCUMENTS 5,483,261 A 1/1996 Yasutake
5,488,204 A 1/1996 Mead et al.
(Continued)

FOREIGN PATENT DOCUMENTS

CN 101493865 7/2009
CN 102151136 8/2011
(Continued)

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.
(Continued)

*Primary Examiner* — Catherine M Voorhees
*Assistant Examiner* — Roland Dinga
(74) *Attorney, Agent, or Firm* — Brownstein Hyatt Farber Schreck, LLP

(57) ABSTRACT

This disclosure relates to methods for measuring one or more physiological signals while the user is engaged in a predetermined activity. Exemplary predetermined activities can include activities such as walking, climbing stairs, biking, and the like. The physiological measurements can include, but are not limited to, heart rate signals. The physiological measurements may be affected by the predetermined activity, so the system may be configured to employ one or more criteria prior to measuring physiological information to minimize the effects. The one or more criteria can include, but are not limited to, an inter-sampling waiting time, continuous motion criteria, predetermined activity criteria, a post-physiological measurement amount of time, and a confidence value. The continuous motion criteria can be based on the type of predetermined activity. For example, walking may have walking state criteria and a step count criteria.

19 Claims, 10 Drawing Sheets

Related U.S. Application Data

(60) Provisional application No. 62/514,437, filed on Jun. 2, 2017.

(51) Int. Cl.

| | | |
|---|---|---|
| *A61B 5/11* | (2006.01) | |
| *A61B 5/0205* | (2006.01) | |
| *A61B 5/021* | (2006.01) | |
| *G16H 20/30* | (2018.01) | |
| *G16H 20/10* | (2018.01) | |
| *G16H 50/70* | (2018.01) | |
| *G16H 40/67* | (2018.01) | |
| *A61B 5/01* | (2006.01) | |

(52) U.S. Cl.
CPC ...... *A61B 5/02416* (2013.01); *A61B 5/02427* (2013.01); *A61B 5/02438* (2013.01); *A61B 5/1118* (2013.01); *A61B 5/1123* (2013.01); *A61B 5/681* (2013.01); *A61B 5/7221* (2013.01); *A61B 5/7271* (2013.01); *G16H 20/10* (2018.01); *G16H 20/30* (2018.01); *G16H 40/67* (2018.01); *G16H 50/70* (2018.01); *A61B 5/0022* (2013.01); *A61B 5/0064* (2013.01); *A61B 5/01* (2013.01); *A61B 5/7203* (2013.01); *A61B 5/7282* (2013.01); *A61B 2503/10* (2013.01)

(58) Field of Classification Search
CPC . A61B 5/02438; A61B 5/1118; A61B 5/1123; A61B 5/681; A61B 5/7221; A61B 5/7271; A61B 5/0022; A61B 5/0064; A61B 5/01; A61B 5/7203; A61B 5/7282; A61B 2503/10; G16H 20/30; G16H 40/67; G16H 50/70; G16H 20/10
See application file for complete search history.

(56) References Cited

U.S. PATENT DOCUMENTS

| | | | |
|---|---|---|---|
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,690,387 B2 | 2/2004 | Zimmerman et al. | |
| 7,015,894 B2 | 3/2006 | Morohoshi | |
| 7,184,064 B2 | 2/2007 | Zimmerman et al. | |
| 7,663,607 B2 | 2/2010 | Hotelling et al. | |
| 8,392,735 B2 | 3/2013 | Mucignat et al. | |
| 8,479,122 B2 | 7/2013 | Hotelling et al. | |
| 9,009,516 B1 | 4/2015 | Gabayan et al. | |
| 10,327,674 B2 | 6/2019 | Hong et al. | |
| 11,166,640 B2 * | 11/2021 | Deng | G16H 50/70 |
| 2004/0015103 A1 * | 1/2004 | Aminian | A61B 5/1127 600/595 |
| 2006/0197753 A1 | 9/2006 | Hotelling | |
| 2013/0324855 A1 * | 12/2013 | Lisogurski | A61B 5/7225 600/476 |
| 2014/0275852 A1 | 9/2014 | Hong et al. | |
| 2016/0029898 A1 | 2/2016 | LeBoeuf et al. | |
| 2016/0038045 A1 | 2/2016 | Shapiro | |
| 2016/0058337 A1 | 3/2016 | Blahnik et al. | |
| 2016/0091952 A1 | 3/2016 | Xu et al. | |
| 2016/0150978 A1 * | 6/2016 | Yuen | A61B 5/0205 600/301 |
| 2016/0324432 A1 | 11/2016 | Ahmed et al. | |
| 2016/0368965 A1 | 12/2016 | Tran | |
| 2016/0374567 A1 * | 12/2016 | Breslow | A61B 5/721 600/301 |
| 2017/0128019 A1 | 5/2017 | Shao et al. | |
| 2017/0188847 A1 | 7/2017 | Ahmed et al. | |
| 2017/0337349 A1 | 11/2017 | Cronin | |
| 2018/0156660 A1 * | 6/2018 | Turgeon | G09G 5/10 |

FOREIGN PATENT DOCUMENTS

| | | |
|---|---|---|
| CN | 105549720 | 5/2016 |
| CN | 105996987 | 10/2016 |
| CN | 106502369 | 3/2017 |
| JP | 2000163031 | 6/2000 |
| JP | 2002342033 | 11/2002 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

PHYSIOLOGICAL SAMPLING DURING PREDETERMINED ACTIVITIES

CROSS REFERENCE TO RELATED APPLICATION

This application is a continuation of U.S. patent application Ser. No. 15/991,798, filed May 29, 2018, which claims the benefit of U.S. Provisional Patent Application No. 62/514,437, filed Jun. 2, 2017, both of which are hereby incorporated by reference it their entirety.

FIELD OF THE DISCLOSURE

This relates to methods for operating photoplethysmogram (PPG) sensors and corresponding systems. More particularly, this disclosure relates to methods and systems configured for heart rate sampling during predetermined activities such as walking.

BACKGROUND OF THE DISCLOSURE

Photoplethysmogram (PPG) sensors can be used to determine physiological information of a user. In a basic form, a PPG system can employ one or more light sources and one or more light detectors. When a PPG sensor unit is positioned such that the one or more light sources and the one or more light detectors are placed against or in proximity to the skin of a user, the one or more light sources can emit light to illuminate the user's skin. The one or more light detectors can receive and measure light that has been transmitted through, reflected by, and/or scattered within and exited the user's tissue. The amount of light measured by the light detectors (e.g., in the form of one or more signals) can vary based on the amount of light absorbed by the user's tissue, and the system can monitor the absorption to calculate one or more physiological parameters, such as a heart rate. As an example, PPG sensor units can measure the timing and/or characteristics of individual heartbeats. The light detector(s) can convert the measured light into an electrical signal indicative of the intensity thereof, and the electrical signal can be converted into a heart rate signal including, for example, the information associated with timing and/or characteristics of the individual heartbeats.

In some instances, the user may be engaging in a predetermined activity. The system can be configured to detect a predetermined activity, where detection of the predetermined activity can begin without requiring user input or initiative. In some examples, it may be useful to have the system measure physiological information during the predetermined activity. Upon detection of the predetermined activity, the system may operate the sensing unit in a predetermined activity mode (i.e., a mode where physiological measurements are taken during the predetermined activity).

SUMMARY OF THE DISCLOSURE

This disclosure relates to methods for measuring one or more physiological signals while the user is engaged in a predetermined activity. Exemplary predetermined activities can include activities such as walking, climbing stairs, biking, and the like. The physiological measurements can include, but are not limited to, heart rate signals. The physiological measurements may be affected by the predetermined activity, so the system may be configured to employ one or more criteria prior to measuring physiological information to minimize the effects. The one or more criteria can include, but are not limited to, an inter-sampling waiting time, continuous motion criteria, predetermined activity criteria, a post-physiological measurement amount of time, and a confidence value. The continuous motion criteria can be based on the type of predetermined activity. For example, walking may have walking state criteria and a step count criteria, biking may have a cadence criteria, and stair climbing may have step count criteria and an altitude criteria.

DETAILED DESCRIPTION

Figure 1:
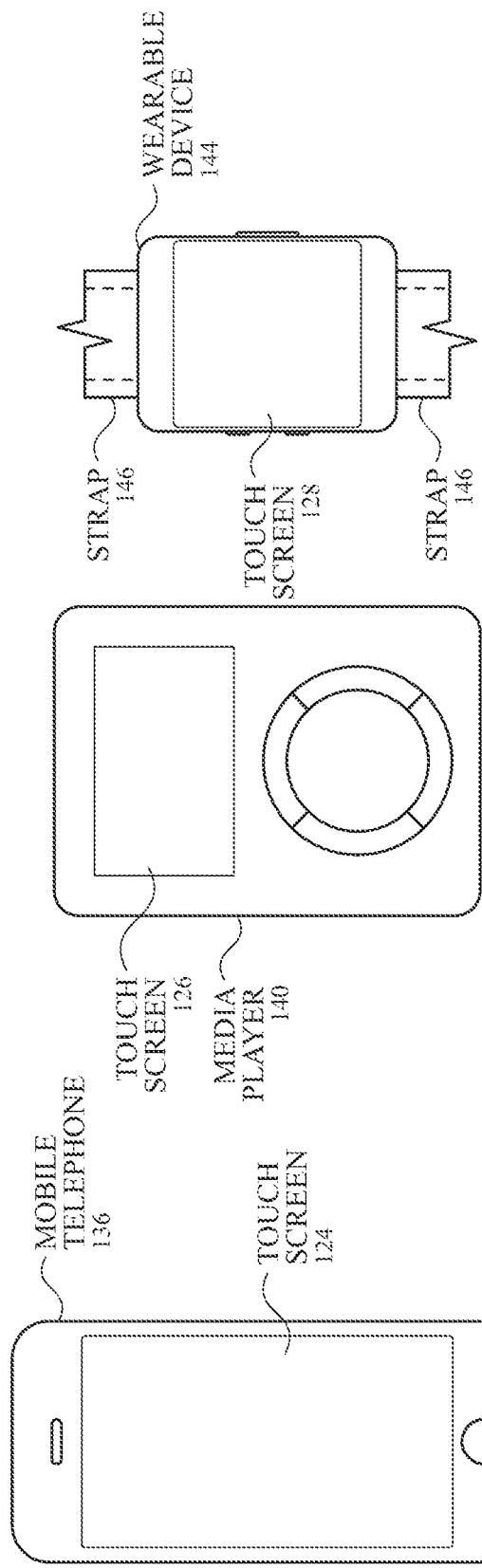
FIGS. 1A-1C illustrate systems in which examples of the disclosure can be implemented.

In the following description of examples, reference is made to the accompanying drawings in which it is shown by way of illustration specific examples that can be practiced. It is to be understood that other examples can be used and structural changes can be made without departing from the scope of the various examples.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Further, although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one-step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

Photoplethysmogram (PPG) sensors can be used to determine physiological information of a user. In a basic form, a PPG sensor unit can employ one or more light sources and one or more light detectors. When a PPG sensor unit is positioned such that the light source(s) and the light detector(s) are placed against or in proximity to the user's skin, the light source(s) can emit light to illuminate the user's skin. The light detector(s) can receive and measure light that has been transmitted through, reflected by, and/or scattered within and exited the user's tissue. The amount of light measured by the light detector(s) (e.g., in the form of one or more signals) can vary based on the amount of light absorbed by the user's tissue, and the system can monitor this absorption to calculate physiological information, such as a heart rate. As an example, a PPG sensor unit can measure the timing and/or characteristics of individual heartbeats. The light detector(s) can convert the measured light into an electrical signal indicative of the intensity thereof, and the electrical signal can be converted into a PPG heart rate signal.

Although examples discussed below are discussed specifically in the context of PPG signals, examples of the disclosure relates to methods for measuring physiological signals and corresponding systems. Exemplary physiological signals and systems include, but are not limited to, heart rate, hear rate variability, pulse oximetry signals, electrocardiography (ECG) signals, impedance cardiography (ICG) signals, and the like.

In some instances, the user may be engaging in a predetermined activity. The system can be configured to detect a predetermined activity, where detection of the predetermined activity can begin without requiring user input or initiative. In some examples, it may be useful to have the system measure physiological information during the predetermined activity. Upon detection of the predetermined activity, the system may operate the sensing unit in a predetermined activity mode (i.e., a mode where physiological measurements are taken during the predetermined activity).

This disclosure relates to methods for measuring one or more physiological signals while the user is engaged in a predetermined activity. Exemplary predetermined activities can include activities such as walking, climbing stairs, biking, and the like. The physiological measurements can include, but are not limited to, heart rate signals. The physiological measurements may be affected by the predetermined activity, so the system may be configured to employ one or more criteria prior to measuring physiological information to minimize the effects (wherein the term "physiological information" is used herein to represent one or more different types of physiological information, one or more data samples of the same type of physiological information, and the like). The one or more criteria can include, but are not limited to, an inter-sampling waiting time, continuous motion criteria, predetermined activity criteria, a post-physiological measurement amount of time, and a confidence value. The continuous motion criteria can be based on the type of predetermined activity. For example, walking may have walking state criteria and a step count criteria, biking may have a cadence criteria, and stair climbing may have step count criteria and an altitude criteria.

Representative applications of methods and apparatus according to the present disclosure are described in this section. These examples are being provided solely to add context and aid in the understanding of the described examples. It will thus be apparent to one skilled in the art that the described examples may be practiced without some or all of the specific details. In other instances, well-known process steps have been described in detail in order to avoid unnecessarily obscuring the described examples. Other applications are possible, such that the following examples should not be taken as limiting.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable system 144 that can include a touch screen 128 and can be attached to a user using a strap 146. The systems of FIGS. 1A-1C can utilize the systems and methods for operating the PPG sensor unit as disclosed.

Figure 2:
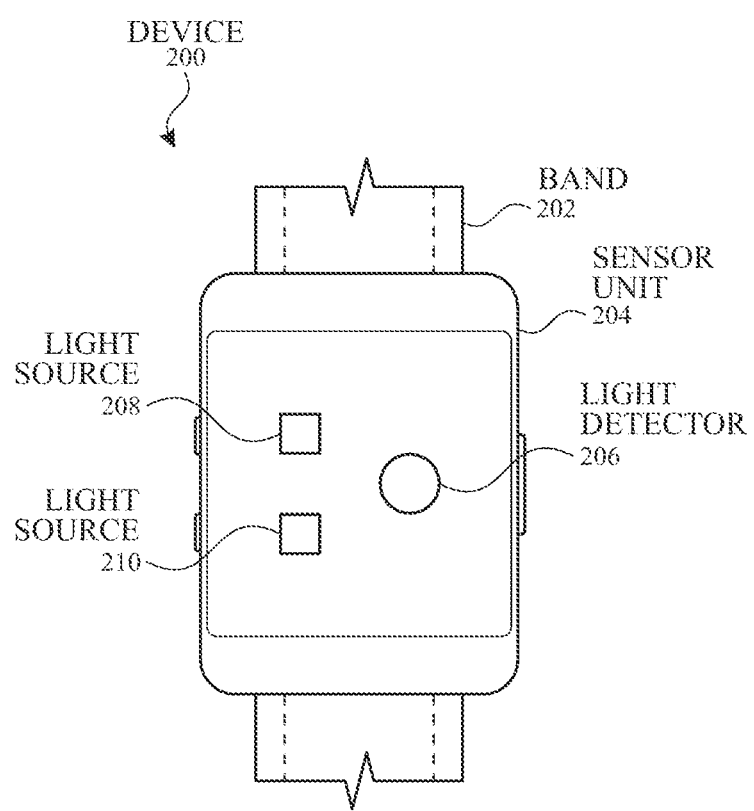
FIG. 2 illustrates a top view of an exemplary electronic system including a light detector and light sources for determining a physiological signal according to examples of the disclosure.

FIG. 2 illustrates a top view of an exemplary electronic system including a light detector and light sources for determining a physiological signal according to examples of the disclosure. Device 200 can include a sensor unit 204 and a band 202, which may be used to couple (e.g., attach) the sensor unit 204 to a portion of a user (e.g., a user's wrist, hand, arm, leg, or the like). The sensor unit 204 can include one or more light sources (e.g., light source 208 and light source 210) and one or more detectors (e.g., light detector 206) located on a surface of device 200. Device 200 and/or sensor unit 204 can be situated such that light sources 208 and 210 and light detector 206 are proximate to the user's skin. For example, device 200 can be held in a user's hand or strapped to a user's wrist, among other possibilities.

Light source 208 and light source 210 can emit light. The emitted light can be incident on the user's skin and can reflect back to be detected by light detector 206. A portion of the emitted light can be absorbed by the user's skin, vasculature, and/or blood, and a portion of the emitted light can be reflected back to light detector 206. In some examples, the light sources can be configured to emit different wavelengths of light. For example, light source 208 can be configured to emit green wavelengths, and light source 210 can be configured to emit infrared wavelengths.

The sensor unit 204 can measure different types of information based on the wavelengths of light. For example, measurements including green wavelengths can be used to determine specific heart rate information, whereas measurements including infrared wavelengths can be used to determined background heart rate information. Examples of the disclosure are not limited to types of measurements from a light source-light detector pair being separate and distinct from types of measurements from another light source-light detector pair. Additionally, examples of the disclosure can include the sensor unit configured to operate with multiple modes, where one mode can include measuring physiological information during predetermined activities. Other modalities can include measuring proximity values, measuring background heart rate, and the like. In some examples, one or more modalities can be deactivated (and others activated) when the predetermined activity is detected. The deactivated one or more modalities can be activated under other circumstances (e.g., during a user-initiated workout).

While FIG. 2 illustrates sensor unit 204 as comprising one light detector and two light sources, examples of the disclosure can include any number of light sources and any number of light detectors. Further, although the figure illustrates the light sources as located on one side (e.g., left side) of device 200 and the light detector as located on the other side (e.g., right side) of device 200, examples of the disclosure can include any configuration and placement of the optical components. The light sources and light detectors discussed throughout the disclosure can include two or more light sources emitting and/or two or more light detectors detecting different wavelengths (or ranges of wavelengths) of light.

The system can be configured to detect a predetermined activity. In some examples, detection of the predetermined activity can begin without requiring user input or initiative. The system can be configured to measure physiological information while the user is engaged in the predetermined activity, where the physiological measurements may be affected by the predetermined activity. Exemplary predetermined activities can include activities involving continuous motion. Continuous motion may be a threshold amount of motion within a window of time, where the thresholds for the amount of motion and the duration of the window may be determined by the system. Exemplary continuous motion can include, but is not limited to, motion resulting from walking, climbing stairs, biking, and the like. The physiological measurements can include, but are not limited to, heart rate signals.

Figure 3A:
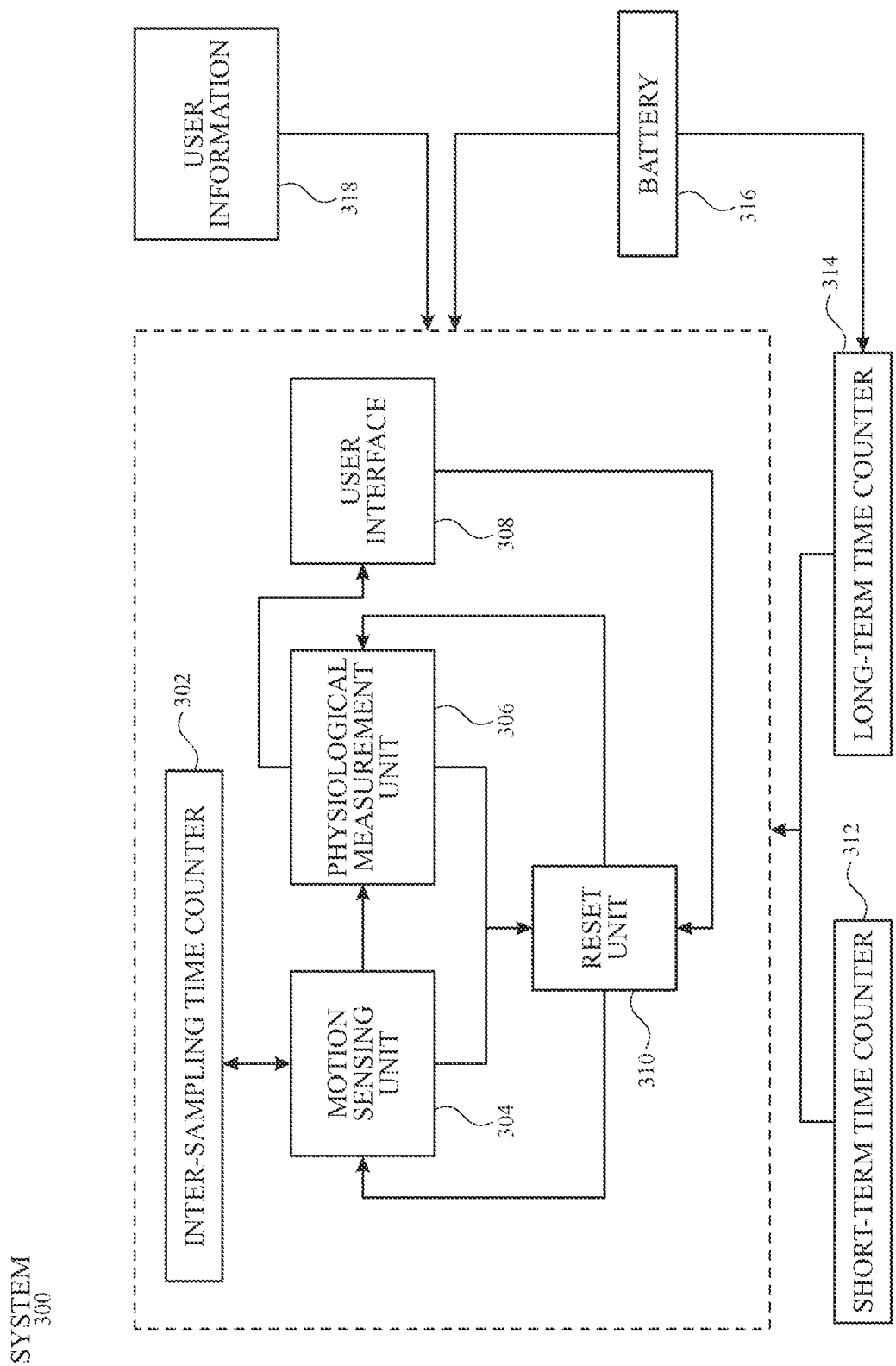
FIG. 3A illustrates a block diagram of an exemplary electronic system according to examples of the disclosure.

In measuring the user's physiological information associated with a predetermined activity, the system 300 can include using one or more units, as illustrated in the exemplary block diagram of FIG. 3A. System 300 can include a battery 316, a short-term time counter 312, and a long-term time counter 314. Short-term time counter 312 and long-term time counter 314 can include discrete logic, a processor, and the like. System 300 can also include storage (not shown) and/or a user interface 308 to store and receive, respectively, user information 318.

The system can further include an inter-sampling time counter 302, a motion sensing unit 304, a physiological measurement unit 306, and a reset unit 310. Each unit can include a processor, which can be a separate processor or a processor shared among multiple units, configured to execute the functionality as described. The motion sensing unit 304 can include one or more sensors configured to measure motion information. For example, the one or more sensors can include an accelerometer. In some examples, the one or more sensors (e.g., infrared optical sensor) can be configured to operate with multiple modes, where one mode includes motion sensing. The physiological measurement unit 306 can include one or more optical components, such as light emitters and light detectors. The reset unit 310 can include discrete logic, a processor, and the like. In some examples, the physiological measurement unit 306 can be configured as a unit separate from the motion sensing unit 304, where the physiological measurement unit 306 may initiate requests to receive motion information from the motion sensing unit 304. In some examples, the motion sensing unit 304 may initiate sending motion information to the physiological measurement unit 306. The motion sensing unit 304 can output the detected activity type of the user and information related to the criteria. In some examples, at least a portion of the motion sensing unit 304 can be integrated with the physiological measurement unit 306.

Figure 3B:
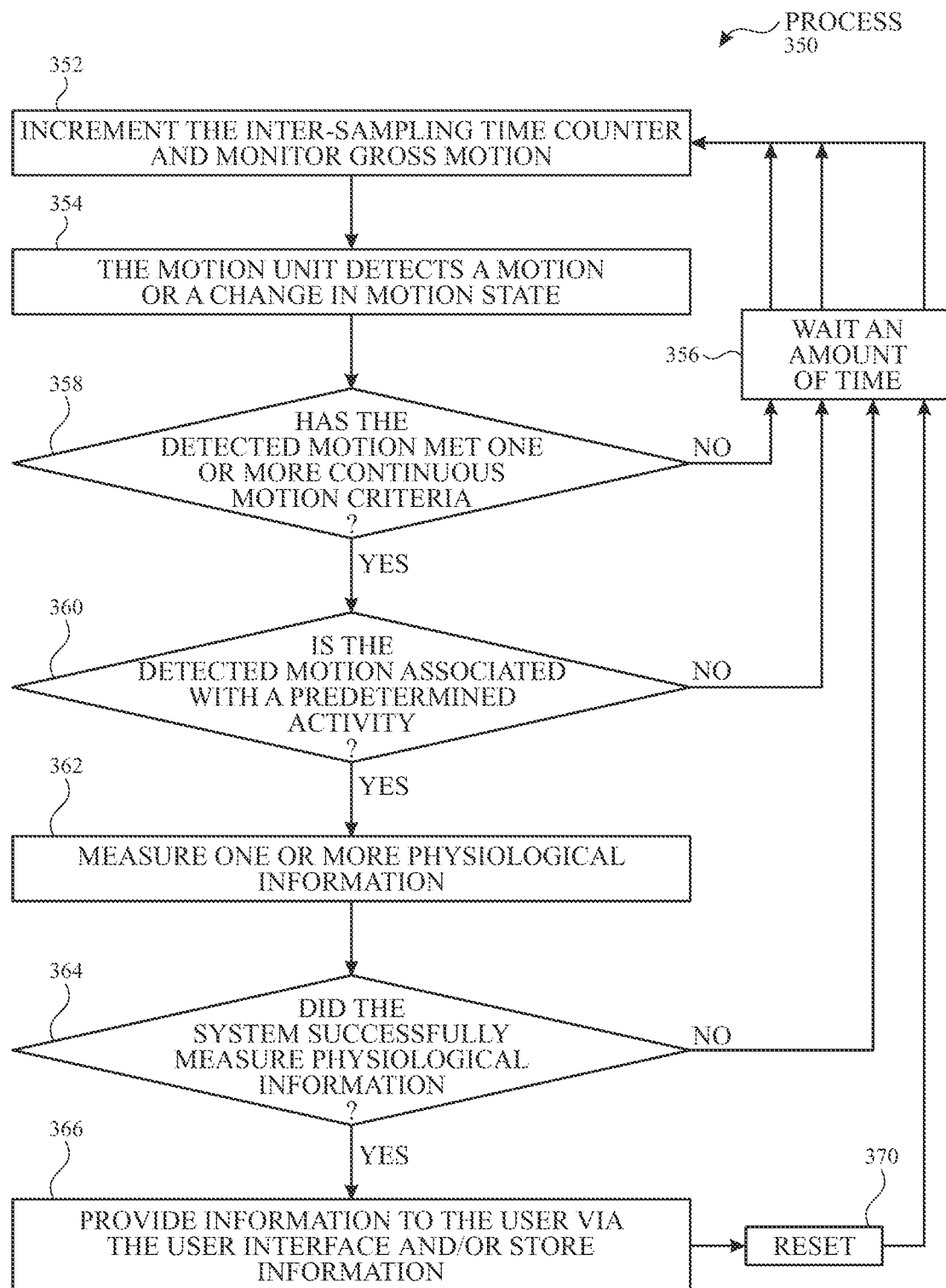
FIG. 3B illustrates an exemplary process for operating a PPG sensing unit in one or more modes according to examples of the disclosure.
Figure 3C:
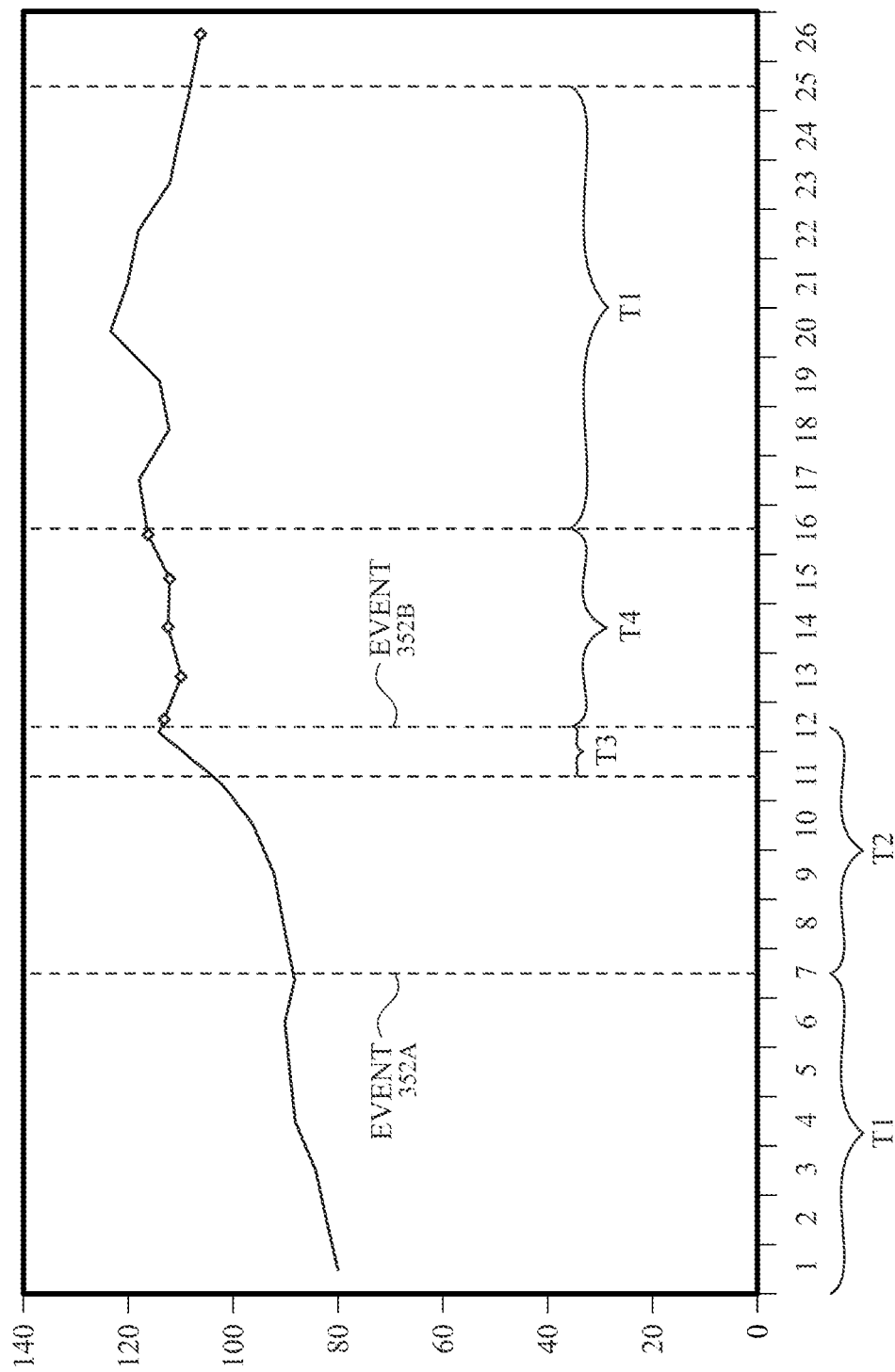
FIG. 3C illustrates an exemplary plot for operating a PPG sensing unit in one or more modes according to examples of the disclosure.

The system can be configured to operate in one or more modes including detecting motion information, measuring physiological information, displaying information on a user interface, and resetting a sampling procedure. FIG. 3B illustrates an exemplary process for operating a PPG sensing unit in one or more modes according to examples of the disclosure. The system can increment the time on the inter-sampling time counter 302 and monitor gross motion (i.e., motion involving muscles to move the user's limb and trunk) via the motion sensing unit 304 (step 352 of process 350). The motion sensing unit 304 can detect a motion or a change in motion state (step 354 of process 350). The motion sensing unit 304 can determine whether the detected motion has met one or more continuous motion criteria (step 358 of process 350). If the detected motion has not met one or more continuous motion criteria, then the system can wait an amount of time (step 356 of process 350), increment the time on the inter-sampling time counter 302, and monitor motion via the motion sensing unit 304 (e.g., step 352). For example, as illustrated in FIG. 3C, the system can set the inter-sampling waiting time equal to the duration of window T1. Any detected motion during window T1 may be ignored.

If the detected motion meets the continuous motion criteria, the motion sensing unit 304 can determine whether the detected motion is associated with at least one predetermined activity (step 360 of process 350). If the detected motion is not associated with the predetermined activity, the system can wait an amount of time (e.g., step 356), increment the time on the inter-sampling time counter 302, and monitor motion via the motion sensing unit 304 (e.g., step 352).

If the detected motion is associated with the predetermined activity, the physiological measurement unit 306 can measure physiological information (step 362 of process 350). If the physiological measurement unit 306 succeeds in measuring physiological information (step 364 of process 350), the system may provide information to the user via a user interface 308 and/or store information (step 366 of process 350). In some instances, the system can execute a reset sampling procedure via reset unit 310 (step 370 of process 350). The system can wait an amount of time (e.g., step 356), where the amount of time can be based on any number of factors such as whether the system successfully measured the physiological information (e.g., at step 364).

In some examples, the physiological measurements may continue for as long as the predetermined activity is detected. In other examples, the physiological measurements may continue after the predetermined activity is no longer detected. The information from the physiological measurements after the predetermined activity is no longer detected can be used for determining information about the user's post-activity state, for example. As one example, the device may start measuring physiological information (e.g., using green light) (e.g., at step 362) once the system determines that the detected motion corresponds to a given predetermined activity (e.g., climbing stairs) (e.g., at step 360). The physiological measurements may continue, either continuously or at predetermined intervals, for a certain time period (e.g., 30 seconds) after motion is no longer detected or detected motion no longer corresponds to the predetermined activity. As another example, the system can take one or more physiological measurements once the motion is no longer detected or detected motion no longer corresponds to the predetermined activity (e.g., a first physiological measurement 15 seconds post-activity and a second physiological measurement 30 seconds post-activity).

The system may wait at least a non-zero period of time before performing a measurement (e.g., inter-sampling wait time at step 352 in FIG. 3B) and/or wait a non-zero amount of time (e.g., at step 356 in FIG. 3B) for the measurement to meet one or more criteria (e.g., motion criteria) are met. For example, the wait time can be configured such that the measurements are spaced apart and do not occur too frequently (e.g., which may drain the battery 316 of the system 300). The wait time can also be configured such that the measurements are spaced close enough together such that the accuracy and sensitivity of the physiological measurements are not compromised. For example, the system can wait after the last PPG measurement (e.g., duration of window T1 illustrated in FIG. 3C) or after determining the user's motion did not correspond to a predetermined activity. Additionally or alternatively, other factors (e.g., confidence value as discussed below) may further delay the initiation of a subsequent measurement. The values waiting times can be adjusted based on one or more factors including, but not limited to, previous measurement attempts, battery life, computational efficiency, and sampling frequency. The waiting times can be predetermined, fixed, and/or dynamically adjusted. In some examples, the motion and/or physiological information can be measured, but may be ignored or discarded. The measured information may instead be used by other components of the systems or for other purposes.

A post-physiological measurement time can be introduced after a physiological measurement (e.g., at step 362). The post-physiological measurement can depend on whether the previous sampling measurement was a successful physiological measurement (i.e., meets physiological criteria). For example, the system may utilize a first post-physiological measurement waiting period (e.g., at step 368 in FIG. 3B) if the physiological measurement was successful and may use a second post-physiological measurement waiting period if the physiological measurement was unsuccessful. In some examples, the second post-physiological measurement waiting period may be shorter than the first post-physiological measurement waiting period. Additionally or alternatively, the post-physiological measurement waiting period may depend on the how long the system took to achieve a successful measurement and/or a confidence value. For example, the post-physiological measurement waiting time may be increased if the system took 90% of the maximum measurement time to achieve a successful measurement compared to if the system took 50% of the maximum measurement time. In some instances, a higher confidence value may indicate a higher probability of the subsequent measurement being a successful measurement, so the post-physiological measurement waiting period may be increased. Similarly, a lower confidence value may indicate a lower probability of the subsequent measurement being a successful measurement, so the post-physiological measurement waiting period may be decreased. Adjusting the post-physiological measurement waiting period can enhance the measurement accuracy and decrease power consumption.

Motion Detection

If a motion is detected (e.g., at step 354) and the inter-sampling waiting time has elapsed (e.g., at step 356), the system can determine whether the detected motion has met one or more continuous motion criteria (e.g., at step 358). The continuous motion criteria can ensure that the user's motion is continuous. The amount of time that the motion is continuous can be greater than or equal to a continuous motion time threshold.

Figure 4A:
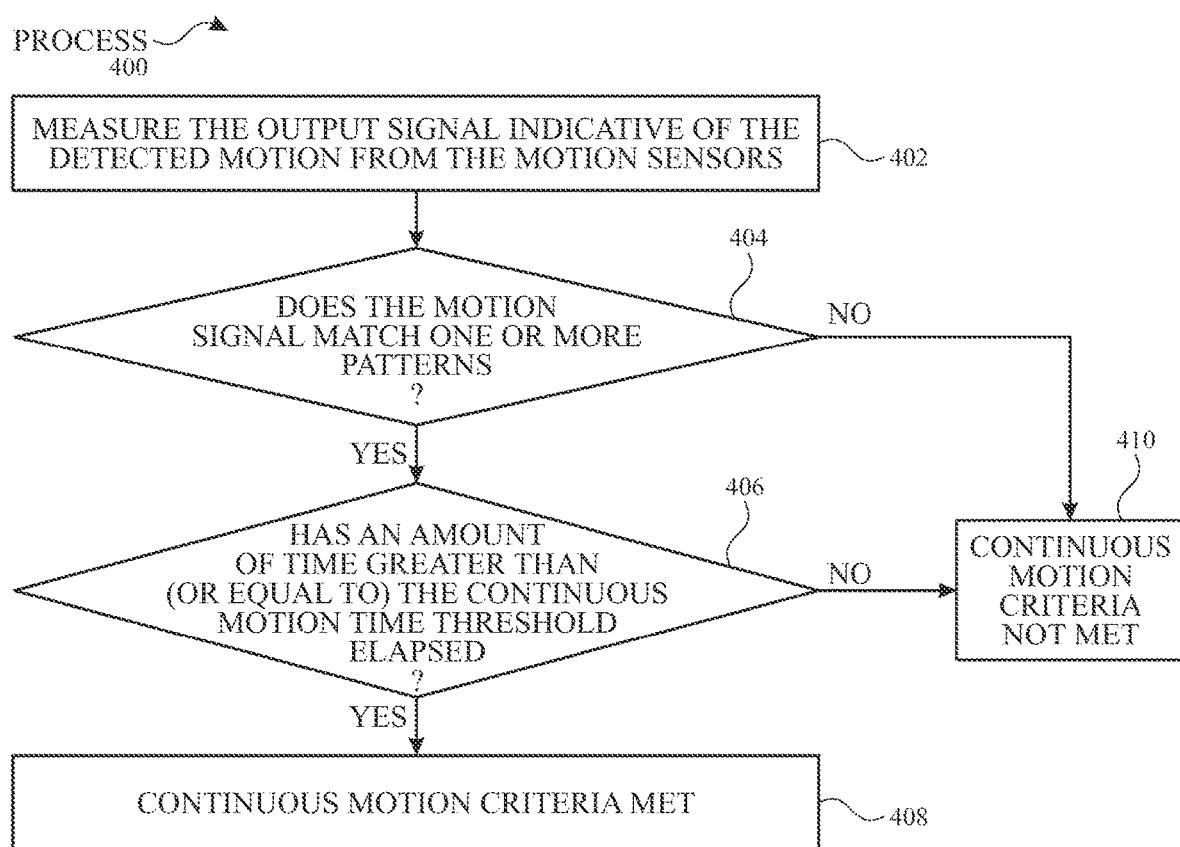
FIG. 4A illustrates an exemplary process for determining whether the user's motion is continuous according to examples of the disclosure.

FIG. 4A illustrates an exemplary process for determining whether the user's motion is continuous according to examples of the disclosure. The motion sensing unit (e.g., motion sensing unit 304 in FIG. 3A) can measure the output signal indicative of the detected motion using one or more sensors (step 402 of process 400). For example, the sensors can include an accelerometer configured to output an acceleration signal. The acceleration signal can be measured periodically. The motion sensing unit can determine if the motion signal matches one or more patterns (step 404 of process 400). For example, the system can determine whether the acceleration signal value is within a certain range of acceleration signal values. The range of acceleration signal values can help bound the user's activity to the predetermined activity. For example, if the predetermined activity is walking, the range of acceleration signal values can be based on predetermined acceleration signal values associated with slow-paced and fast-paced walking. An acceleration signal value higher than the range may indicate that the user's activity has changed to running, and an acceleration signal value lower than the range may indicate that the user's activity has changed to sitting, for example. In some examples, the range of acceleration signal values may be determined after a predetermined amount of time where the user's motion is present has elapsed. For example, at event 352B illustrated in FIG. 3C, the system can wait for the end of window T3 (e.g., 30 seconds) in order to allow for the user's heart rate to reach steady state. The range of acceleration signal values may be determined based on a certain percentage greater than and less than the acceleration signal value measured at event 352B.

If the acceleration signal value is within the range, the continuous motion time threshold can be used to determine whether the user is continuously engaged in the predetermined activity. Ensuring that the user is continuously engaged in the predetermined activity can help prevent inaccurate measurements due to, e.g., noise or sporadic user motion. In some instances, the continuous motion time threshold can provide a time buffer to allow the user's heart rate to increase (or decrease) to reach steady state. The motion sensing unit can determine if an amount of time greater than (or equal to) the continuous motion time threshold has elapsed (step 406 of process 400). If the amount of time is greater than (or equal to) the continuous motion time threshold, the continuous motion criteria can be met (step 408 of process 400).

For example, as illustrated in FIG. 3C, the system can detect a change in motion state at event 352A. After the change in motion state is detected, the system may wait the duration of window T2 as the user's heart rate increases (e.g., in response to the user's change in motion state). In some instances, any measurements during window T2 may lead to inaccurate physiological information. During window T2, the system may not utilize (e.g., ignore, discard, etc.) measurements from the physiological measurement unit (e.g., physiological measurement unit 306) in its determination of physiological information. In some instances, at event 352B, the physiological measurement unit may switch modes (e.g., configured for proximity and/or background heart rate sensing prior to event 352B and configured for physiological sampling during predetermined activities after event 352B). Although the sensors may be activated (e.g., turned on) in some instances, the system may delay the determination of whether the continuous motion criteria are met until the start of window T3.

The continuous motion time threshold can be equal to the duration of window T3. During window T3 (i.e., continuous motion time period), the motion sensing unit can check that the user's motion is the same as the predetermined activity by periodically determining whether the measured motion information (e.g., acceleration signals) match one or more motion patterns (e.g., acceleration signal values), as discussed above. If the acceleration signal values fall outside the range of acceleration signal values at any time during window T3, the continuous motion criteria may not be satisfied (step 410 of process 400). In some instances, the system can wait an amount of time before returning to a motion measurement and determining whether the measured motion meets the continuous motion criteria. Additionally or alternatively, the system can set/adjust the continuous motion criteria thresholds.

Predetermined Activity

If the detected motion meets the continuous motion criteria (e.g., at step 358), the motion sensing unit can determine whether the detected motion is associated with a predetermined activity (e.g., at step 360). In some examples, determining whether the detected motion is associated with a predetermined activity can be included in determining whether the detected motion has met one or more continuous motion criteria. In some examples, the determination related to the predetermined activity can be separate from the determination related to continuous motion. For example, multiple activities (e.g., running compared to jumping) may be associated with similar ranges of gross motion signal values (used in the determination of continuous motion), but may be different activities that can be differentiated using one or more other sensors (e.g., GPS).

Steps for determining whether the detected motion is associated with a predetermined activity can differ depending on the predetermined activity. Exemplary predetermined activities can include, but are not limited to, walking, biking, and stair climbing. For example, walking may have one or more criteria, such as walking state criteria (e.g., the distance the user has moved, the amount of movement measured by a sensor, etc.) and a step count criteria. Biking may have cadence criteria (and an associated determination of whether the measured cadence meets the cadence criteria). In some examples, the measured motion information can be used to determine a pedaling criteria, which can be compared to one or more threshold values (e.g., number of occurrences of a given frequency of rotation). Stair climbing may have step count criteria and altitude criteria (and an associated determination of whether the measured altitude meets the altitude criteria). In some examples, the measured motion information can be used to determine a change in altitude, which can be compare to one or more threshold values (e.g., number of steps of a given change in altitude, the total change in altitude for all steps, etc.). The change in altitude can be compared to one or more threshold altitude-related values.

Figure 4B:
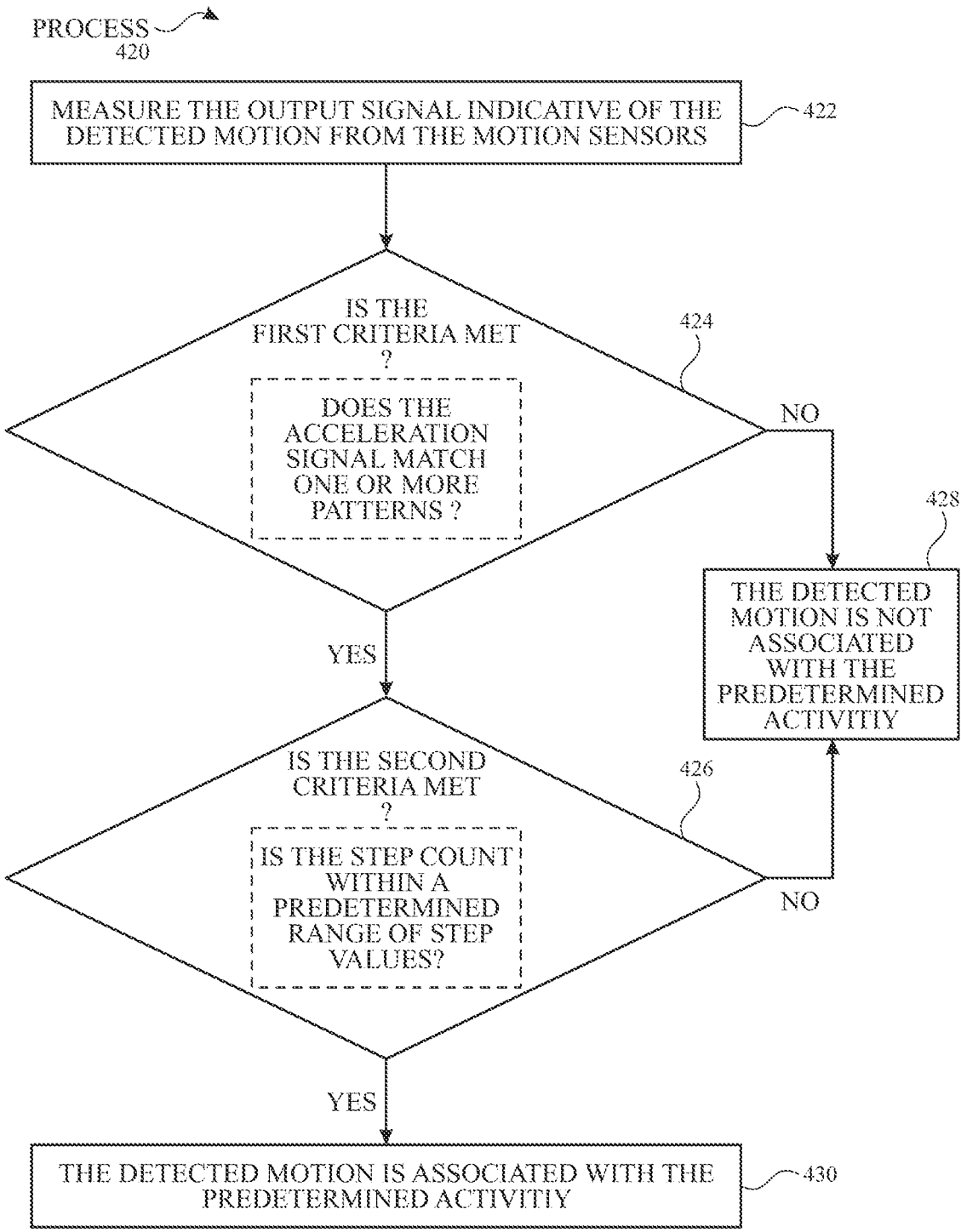
FIG. 4B illustrates an exemplary process for determining whether a detected motion is associated with a predetermined activity according to examples of the disclosure.

FIG. 4B illustrates an exemplary process for determining whether the detected motion is associated with a predetermined activity according to examples of the disclosure. The motion sensing unit (e.g., motion sensing unit 304 in FIG. 3A) can measure the output signal indicative of the detected motion from the sensors (step 422 of process 420). For example, the sensors can include an accelerometer configured to output an acceleration signal. The acceleration signal can be measured periodically. Other exemplary sensors can include, but are not limited to, gyroscopes, altimeters, and the like. In some examples, the output signal in step 422 can be the same output signal from step 402 in process 400 in FIG. 4A.

The motion sensing unit can determine whether the first criteria are met (step 424 of process 420). For example, for walking, the first criteria can be the walking state criteria. The motion sensing unit can determine whether the acceleration signal matches one or more patterns (e.g., the acceleration signal value is within a range of acceleration signal values). If the first criteria are met, then the motion sensing unit can determine whether the second criteria are met (step 426 of process 420). For example, for walking, the second criteria can be the step count criteria. The motion sensing unit can determine if the step count (e.g., the number of steps per second) is within a range of step count values. If the first criteria is not met (e.g., the acceleration signal value is not within a predetermined range of acceleration signal values) and/or the second criteria is not met (e.g., the step count is not within a predetermined range of step count values), then the system can determine that the detected motion is not associated with the predetermined activity (step 428 of process 420). Otherwise, the system can determine that the motion is associated with the predetermined activity (step 430 of process 420). Although FIG. 4B illustrates criteria for walking, examples of the disclosure include criteria for other predetermined activities, as discussed above. Additionally, the criteria and/or predetermined ranges can be based on one or more factors such as user's health condition, the user's characteristics, and historical data (e.g., from user information 318 in FIG. 3A).

In some examples, determining whether the detected motion is associated with the predetermined activity can be based on information from a preceding time window. For example, as illustrated in FIG. 3C, the preceding time window can be window T3 (e.g., 30 seconds) before event 352B. As discussed below, event 352B can correspond to operating the physiological measurement unit in a predetermined activity mode (i.e., a mode where physiological measurements are taken during the predetermined activity).

Physiological Measurements

In some instances, the system can wait to switch the mode (e.g., measuring physiological information during a predetermined activity) of the optical sensors included in the physiological measurement unit (e.g., physiological measurement unit 306 in FIG. 3A) until determining that the detected motion corresponds to the predetermined activity. Prior to the determination, the optical sensors can be configured to operate in different modes (e.g., measuring background heart rate).

Figure 4C:
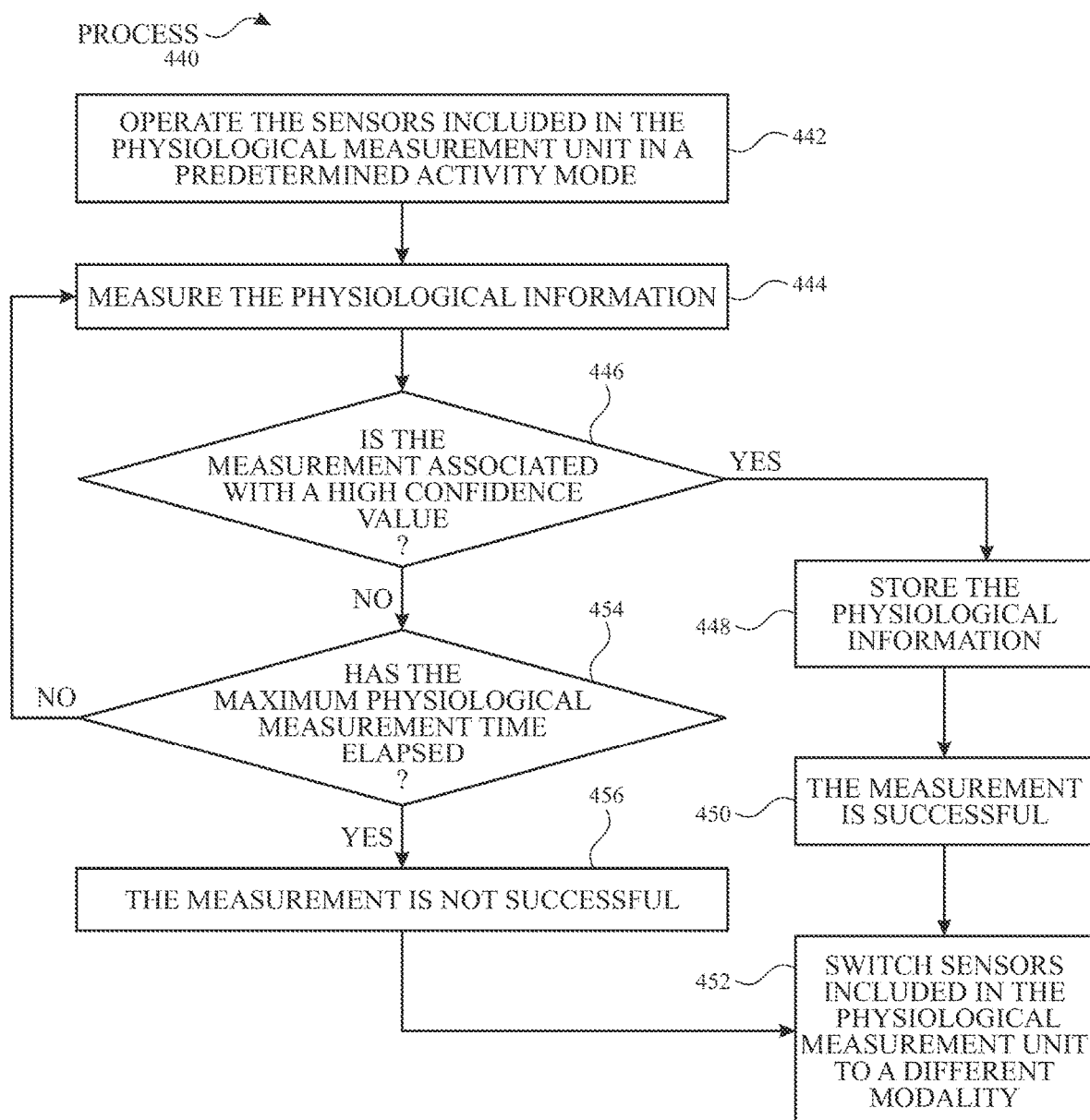
FIG. 4C illustrates an exemplary process for measuring physiological information based on a confidence value according to examples of the disclosure.

If the detected motion corresponds to the predetermined activity (e.g., at step 360), the system can measure physiological information (e.g., at step 362). FIG. 4C illustrates an exemplary process for measuring physiological information according to examples of the disclosure. The modality of the sensors included in the physiological measurement unit can be switched (e.g., to measure physiological information during the predetermined activity) (step 442 of process 440), and the physiological information can be measured (step 444 of process 440). For example, as illustrated in FIG. 2, the system can operate the light source 208, the light source 210, and the light detector 206 in a predetermined activity mode. The predetermined activity mode can correspond to event 352B in FIG. 3C. The sensors can be configured to measure physiological information until a successful measurement is taken or a maximum physiological measurement time (e.g., the entirety of window T4 in FIG. 3C) has elapsed, whichever occurs first.

If a physiological measurement is taken with a high confidence value (i.e., the confidence value meets a predetermined confidence threshold) (step 446 of process 440), then the system may store physiological information (step 448 of process 440). In some examples, when the confidence value meets the confidence threshold, the measurement is a successful measurement (step 450 of process 440). If the physiological measurement does not have a high confidence value, the physiological measurement unit can continue measuring the physiological information (e.g., at step 444) until the maximum physiological measurement time has elapsed (step 454 of process 440). If the maximum physiological measurement time has elapsed, then the system may determine that the measurement was not successful (step 456 of process 440). The maximum physiological measurement time can be based on one or more factors, such as confidence value and battery life.

Examples of the disclosure can further include adjusting the operating conditions (e.g., increasing the intensity of the light sensors) and/or activating additional sensors if the measurement is initially deemed unsuccessful, and attempting subsequent measurements with the adjusted operating conditions. As discussed above, the post-physiological measurement time (e.g., at step 368) can differ depending on whether the physiological measurement was successful. Whether the measurement is successful or not, the sensors included in the physiological measurement unit can be switched to a different modality (step 452 of process 440).

Reset Procedure

When the system resets (e.g., at step 370), the system may reset one or more timers such as the inter-sampling time counter (e.g., inter-sampling time counter 302 in FIG. 3A) and/or criteria (e.g., one or more thresholds may be returned to default values). In some examples, the system may wait at least a reset period before a subsequent motion and/or physiological measurement. In some examples, the system can continue the measurements and can optionally discard or ignore the measurements. In some instances, the system may measure motion information before the reset period and then measure physiological information after the reset period. In some instances, the reset procedure may follow after a certain occurrence. The occurrence can include a certain number of events occurring, a certain time window has elapsed (including a certain number of events occurring within the time window), and/or a certain number of measurements that meet the continuous motion criteria. For example, the user may be walking continuously for 30 minutes. After 5 minutes of detection of the continuous walking, the system may execute the reset procedure.

In some instances, the duration of the reset period may depend on one or more conditions such as battery level and time of day. Additionally or alternatively, the reset period may be adjusted to provide an average rate of motion measurements and/or average rate of physiological measurements. For example, the reset period may be adjusted to provide an average sampling rate less than or equal to one physiological measurement per hour (which may in turn depend on factors such as battery life). If, for example, four physiological measurements were taken over the course of a certain time period (e.g., an hour) before the reset is initiated, the system may wait an additional amount of time (e.g., three hours) before attempting another physiological measurement.

The system may initiate a new round of motion and/or physiological measurements after the reset period has elapsed. In some instances, the system may look for one or more initiation criteria to be met before initiating the new round of primary measurements. For example, in some instances the system may initiate a new round of measurements if the user changes motion state. In some instances, one or more conditions may cause the reset. For example, the reset procedure may be executed when a certain (e.g., predetermined threshold) number of physiological measurements are unsuccessful.

Short-Term and Long-Term Time Counters

The system can include a short-term time counter (e.g., short-term time counter 312 in FIG. 3A) and/or a long-term time counter (e.g., long-term time counter 314 in FIG. 3A). Both counters can be configured to reduce the likelihood of the system measuring physiological information too frequently and to help spread the physiological measurements out through the course of a given time period (e.g., an hour, a day, or between charging periods). For example, the short-term time counter can be configured to count and aggregate the amount of time the system spends performing a measurement within an hour. The amount of time spent measuring physiological information and/or activating the sensors included in the physiological measurement unit may be added (or subtracted) from the short-term time counter. Once the short-term time threshold (e.g., an hourly budget) is reached (or exceeded), the system may delay further physiological measurements until the short-term time counter is reset at respective time intervals (e.g., hour).

In some examples, these delayed physiological measurements may be those measurements begin in response to a detected predetermined activity. In some instances, the system may take one or more physiological measurements in response to other factors, even if the short-term time threshold is reached. Exemplary factors include, but are not limited to, the user beginning a different type of activity (e.g., exercise), the user manually requesting a measurement via touch input, an application initiating the measurement, and the like.

The long-term time counter can be configured to count and aggregate the amount of time measured within a longer time period (e.g., within a day) than the short-term time counter. The long-term time counter may be reset every day (or every time the battery is recharged), for example. The amount of time spent measuring physiological information and/or activating the sensors may be added (or subtracted) from both the short-term and long-term time counters. In some examples, the amount of time that the sensing unit is used for other modalities can be accounted for the short-term and/or long-term time counters.

Primary and Secondary Measurements

The system can be configured to perform different types of measurements in some or all of the above examples: primary and secondary measurements. The primary measurements can include readings using a first set of operating conditions of the physiological measurement unit, and the secondary measurements can use a different, second set of operating conditions of the physiological measurement unit. For example, the primary measurements may be more accurate and/or less sensitive to noise than the secondary measurements, but may consume more power. In these instances, the system may be able to perform frequent secondary measurements, but may wish to restrict the number of instances (e.g., less frequent) in which the primary measurements are used to reduce the strain on the battery (e.g., battery 316 in FIG. 3A). The system can determine the battery life and select between primary or secondary measurements based on the battery life. That is, the system can switch between different operating conditions of the physiological measurement unit, wherein the operating conditions may be based on one or more factors such as battery life.

As an example, the secondary measurements may be taken using a light source having a different wavelength (or wavelength range) from that of the primary measurement. For example, secondary measurements (e.g., using lower power infrared light sources and emitters) can be used to measure background heart rate. When (e.g., following a reset of the sample procedure) the physiological measurement unit is switched to operate with the modality for physiological measurements during predetermined activities within a given window (e.g., for the given day), the system can dynamically switch over to measuring the heart rate using primary measurements (e.g., using higher accuracy light sources and emitters operating in the green wavelengths). Other subsequent instances of activating the physiological measurement unit within the same given window may utilize the primary measurements.

In some instances, one type of measurement can be taken prior to one or more criteria being met, and the system can switch to the other type of measurement once the criteria are met. For example, the sensing unit can be configured to operate in a first range of wavelengths before the criteria are met, then switch to operating in a second range of wavelength when the criteria are met.

Figure 5:
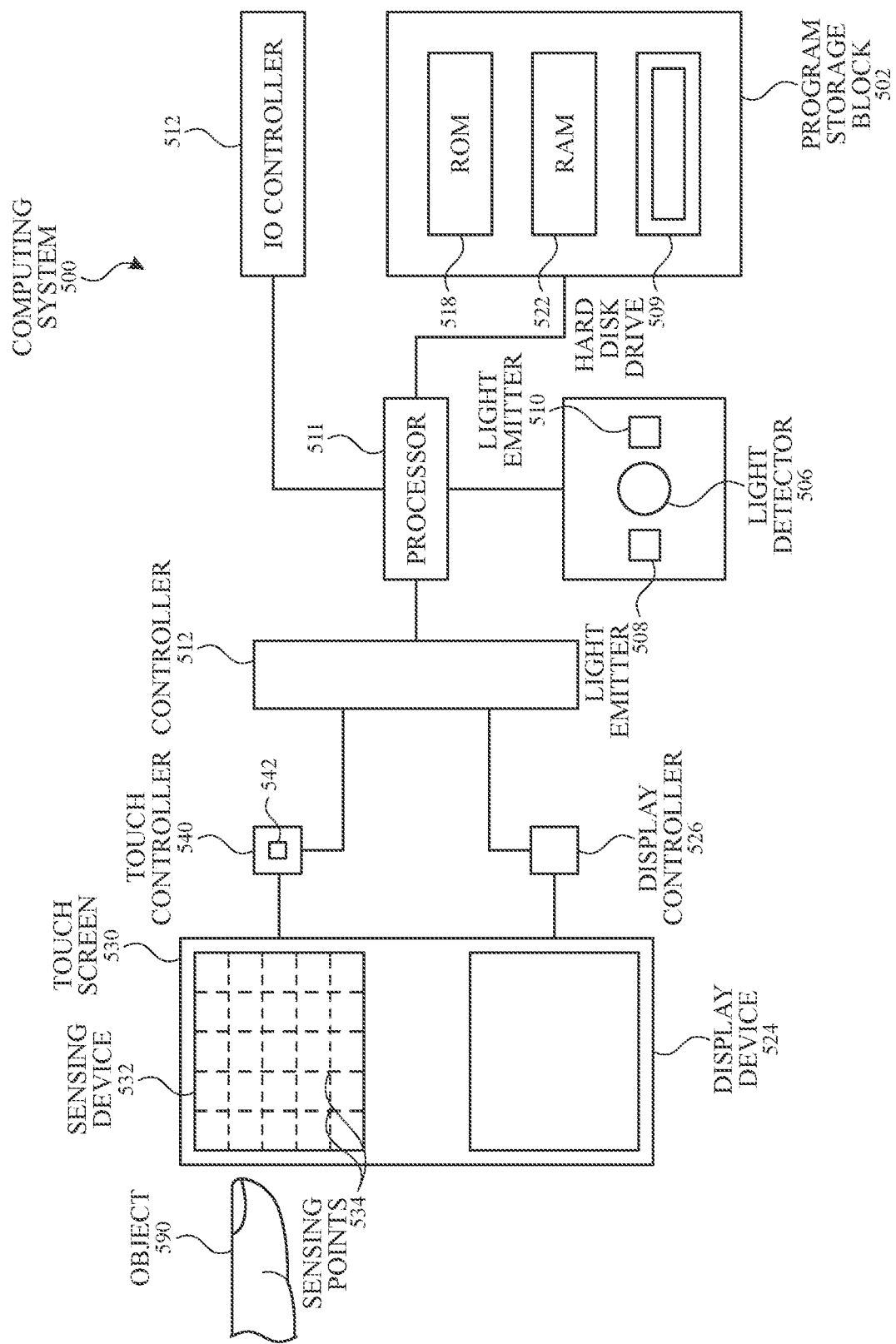
FIG. 5 illustrates an exemplary block diagram of a computing system comprising a PPG sensor unit according to examples of the disclosure.
Figure 6:
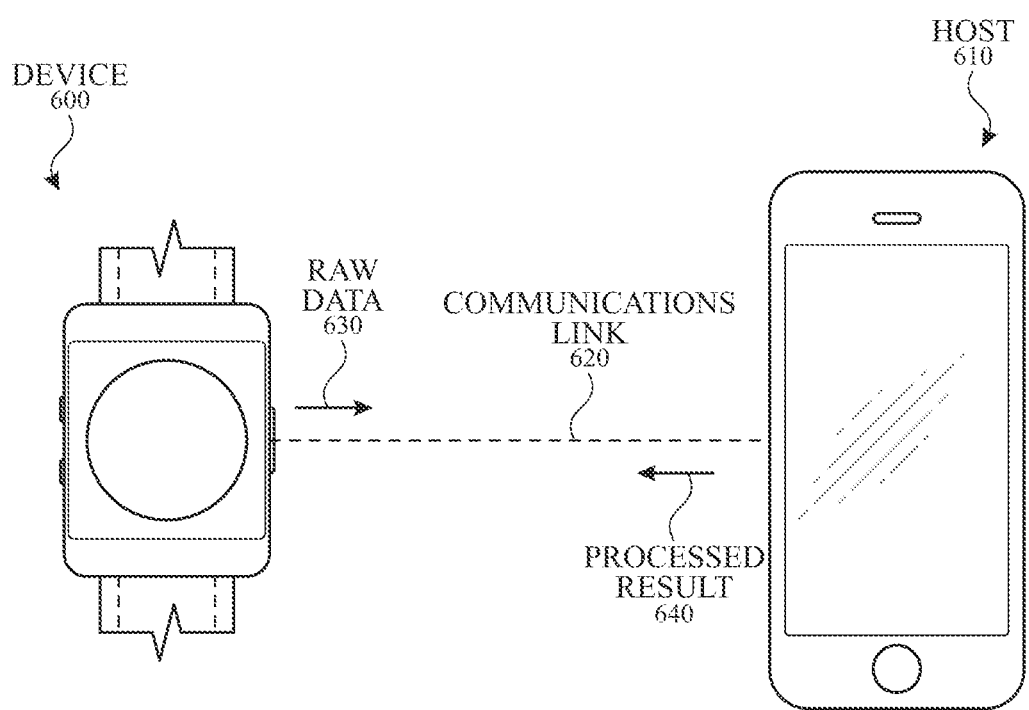
FIG. 6 illustrates an exemplary configuration in which a system is connected to a host according to examples of the disclosure.

FIG. 5 illustrates an exemplary block diagram of a computing system comprising a PPG sensor unit according to examples of the disclosure. Computing system 500 can correspond to any of the computing systems illustrated in FIGS. 1A-1C. Computing system 500 can include a processor 511 configured to execute instructions and to carry out operations associated with computing system 500. For example, using instructions retrieved from memory, processor 511 can control the reception and manipulation of input and output data between components of computing system 500. Processor 511 can be a single-chip processor or can be implemented with multiple components.

In some examples, processor 511 together with an operating system can operate to execute computer code and produce and use data. The computer code and data can reside within a program storage block 502 that can be operatively coupled to processor 511. Program storage block 502 can generally provide a place to hold data that is being used by computing system 500. Program storage block 502 can be any non-transitory computer-readable storage medium (excluding signals), and can store, for example, history and/or pattern data relating to signal values measured by one or more light detectors such as light detector 504. By way of example, program storage block 502 can include Read-Only Memory (ROM) 518, Random-Access Memory (RAM) 522, hard disk drive 509 and/or the like. The computer code and data could also reside on a removable storage medium and loaded or installed onto the computing system 500 when needed. Removable storage mediums include, for example, CD-RM, DVD-ROM, Universal Serial Bus (USB), Secure Digital (SD), Compact Flash (CF), Memory Stick, Multi-Media Card (MMC) and a network component.

Computing system 500 can also include an input/output (I/O) controller 512 that can be operatively coupled to processor 511 or it may be a separate component as shown. I/O controller 512 can be configured to control interactions with one or more I/O systems. I/O controller 512 can operate by exchanging data between processor 511 and the I/O systems that desire to communicate with processor 511. The I/O systems and I/O controller 512 can communicate through a data link. The data link can be a one way link or a two way link. In some cases, I/O systems can be connected to I/O controller 512 through wireless connections. By way of example, a data link can correspond to PS/2, USB, Firewire, IR, RF, Bluetooth or the like.

Computing system 500 can include a display system 524 that can be operatively coupled to processor 511. Display system 524 can be a separate component (peripheral system) or can be integrated with processor 511 and program storage block 502 to form a desktop computer (all in one machine), a laptop, handheld or tablet computing system of the like. Display system 524 can be configured to display a graphical user interface (GUI) including perhaps a pointer or cursor as well as other information to the user. By way of example, display system 524 can be any type of display including a liquid crystal display (LCD), an electroluminescent display (ELD), a field emission display (FED), a light emitting diode display (LED), an organic light emitting diode display (OLED) or the like.

Display system 524 can be coupled to display controller 526 that can be coupled to processor 511. Processor 511 can send raw data to display controller 526, and display controller 526 can send signals to display system 524. Data can include voltage levels for a plurality of pixels in display system 524 to project an image. In some examples, processor 511 can be configured to process the raw data.

Computing system 500 can also include a touch screen 530 that can be operatively coupled to processor 511. Touch screen 530 can be a combination of sensing system 532 and display system 524, where the sensing system 532 can be a transparent panel that is positioned in front of display system 524 or integrated with display system 524. In some cases, touch screen 530 can recognize touches and the position and magnitude of touches on its surface. Touch screen 530 can report the touches to processor 511, and processor 511 can interpret the touches in accordance with its programming. For example, processor 511 can perform tap and event gesture parsing and can initiate a wake of the system or powering on one or more components in accordance with a particular touch.

Touch screen 530 can be coupled to a touch controller 540 that can acquire data from touch screen 530 and can supply the acquired data to processor 511. In some cases, touch controller 540 can be configured to send raw data to processor 511, and processor 511 processes the raw data. For example, processor 511 can receive data from touch controller 540 and can determine how to interpret the data. The data can include the coordinates of a touch as well as pressure exerted. In some examples, touch controller 540 can be configured to process raw data itself. That is, touch controller 540 can read signals from sensing points 534 located on sensing system 532 and turn them into data that the processor 511 can understand.

Touch controller 540 can include one or more microcontrollers such as microcontroller 542, each of which can monitor one or more sensing points 534. Microcontroller 542 can, for example, correspond to an application specific integrated circuit (ASIC), which works with firmware to monitor the signals from sensing system 532, process the monitored signals, and report this information to processor 511.

One or both display controller 526 and touch controller 540 can perform filtering and/or conversion processes. Filtering processes can be implemented to reduce a busy data stream to prevent processor 511 from being overloaded with redundant or non-essential data. The conversion processes can be implemented to adjust the raw data before sending or reporting them to processor 511.

In some examples, sensing system 532 is based on capacitance. When two electrically conductive members come close to one another without actually touching, their electric fields can interact to form a capacitance. The first electrically conductive member can be one or more of the sensing points 534, and the second electrically conductive member can be an object 590 such as a finger. As object 590 approaches the surface of touch screen 530, a capacitance can form between object 590 and one or more sensing points 534 in close proximity to object 590. By detecting changes in capacitance at each of the sensing points 534 and noting the position of sensing points 534, touch controller 540 can recognize multiple objects, and determine the location, pressure, direction, speed, and acceleration of object 590 as it moves across the touch screen 530. For example, touch controller 540 can determine whether the sensed touch is a finger, tap, or an object covering the surface.

Sensing system 532 can be based on self-capacitance or mutual capacitance. In self-capacitance, each of the sensing points 534 can be provided by an individually charged electrode. As object 590 approaches the surface of the touch screen 530, the object can capacitively couple to those electrodes in close proximity to object 590, thereby stealing charge away from the electrodes. The amount of charge in each of the electrodes can be measured by the touch controller 540 to determine the position of one or more objects when they touch or hover over the touch screen 530. In mutual capacitance, sensing system 532 can include a two layer grid of spatially separated lines or wires, although other configurations are possible. The upper layer can include lines in rows, while the lower layer can include lines in columns (e.g., orthogonal). Sensing points 534 can be provided at the intersections of the rows and columns. During operation, the rows can be charged, and the charge can capacitively couple from the rows to the columns. As object 590 approaches the surface of the touch screen 530, object 590 can capacitively couple to the rows in close proximity to object 590, thereby reducing the charge coupling between the rows and columns. The amount of charge in each of the columns can be measured by touch controller 540 to determine the position of multiple objects when they touch the touch screen 530.

Computing system 500 can also include one or more light emitters such as light emitters 508 and 510 and one or more light detectors such as light detector 506 proximate to skin of the user. Light emitters 508 and 510 can be configured to generate light, and light detector 506 can be configured to measure a light reflected or absorbed by skin, vasculature, and/or blood of the user. Light detector 506 can send measured raw data to processor 511, and processor 511 can perform noise cancellation to determine the signal. Processor 511 can dynamically activate light emitters and/or light detectors based on an application, user skin type, and usage conditions. In some examples, some light emitters and/or light detectors can be activated, while other light emitters and/or light detectors can be deactivated to conserve power, for example. In some examples, processor 511 can store the raw data and/or processed information in a ROM 518 or RAM 522 for historical tracking or for future diagnostic purposes.

In some examples, the light detector(s) can measure light information and a processor can determine a signal from the reflected, scattered, and/or absorbed light. Processing of the light information can be performed on the system as well. In some examples, processing of light information need not be performed on the system itself. FIG. 7 illustrates an exemplary configuration in which a system is connected to a host according to examples of the disclosure. Host 710 can be any system external to system 700 including, but not limited to, any of the systems illustrated in FIGS. 1A-1C or a server. System 700 can be connected to host 710 through communications link 720. Communications link 720 can be any connection including, but not limited to, a wireless connection and a wired connection. Exemplary wireless connections include Wi-Fi, Bluetooth, Wireless Direct, and Infrared. Exemplary wired connections include Universal Serial Bus (USB), FireWire, Thunderbolt, or any connection requiring a physical cable.

In operation, instead of processing light information from the light detectors on the system 700 itself, system 700 can send raw data 730 measured from the light detectors over communications link 720 to host 710. Host 710 can receive raw data 730, and host 710 can process the light information. Processing the light information can include canceling or reducing any noise due to artifacts and determining physiological signals such as a user's heart rate. Host 710 can include algorithms or calibration procedures to account for differences in a user's characteristics affecting signal. Additionally, host 710 can include storage or memory for tracking a signal history for diagnostic purposes. Host 710 can send the processed result 740 or related information back to system 700. Based on the processed result 740, system 700 can notify the user or adjust its operation accordingly. By offloading the processing and/or storage of the light information, system 700 can conserve space and power enabling system 700 to remain small and portable, as space that could otherwise be required for processing logic can be freed up on the system.

In some examples, registering the instance can include sending information related to the PPG signal(s) to the system 700 (e.g., a watch). System 700 may display at least a portion of the information on the interface (e.g., interface 508 illustrated in FIG. 5B) and may send at least a portion of the information (e.g., as raw data 730) to host 710 (e.g., a mobile telephone) via communications link 720. The portion of the information sent to the host 710 can include the same or different information displayed by system 700.

One aspect of the present technology is measuring, gathering, and using data available from various sources to improve methods and systems for heart rate sampling during predetermined activities. The present disclosure contemplates that, in some instances, this gathered data may include personal information data that uniquely identifies or can be used to contact or locate a specific person. Additionally, the measured information can be delivered to the user, where additional information can be utilized to improve the delivery of measured information, analysis, or any other content that may be of interest to the users. Such personal information data can include demographic data, location-based data, telephone numbers, email addresses, twitter ID's, home addresses, data or records related to a user's health or level of fitness (e.g., vital signs measurements, medication information, exercise information), date of birth, user preferences, or any other identifying or personal information.

The present disclosure recognizes that the use of such personal information data, in the present technology, can be used to the benefit of users. For example, the personal information data can be used to deliver heart rate sampling and/or predetermined activity information that is of greater interest to the user. Accordingly, use of such personal information data can be to enable timely and controlled delivery of the measured information, analysis, or other content to the user. Further, other uses for personal information that benefit the user are also contemplated by the present disclosure. For instance, health and fitness data may be used to provide insights into a user's general wellness, or may be used as positive feedback to individuals using technology to pursue wellness goals.

In some examples, an entity may use the personal information for collecting, analyzing, disclosing, measuring, transferring, and/or storing the measured information, analysis, or other user-specific content. The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users and should be updated as the collection and/or use of data changes. Personal information from users should be collected for legitimate and reasonable uses of the entity and not shared (e.g., sold) outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. These privacy policies and/or privacy practices can be generally recognized as meeting (or exceeding) industry or governmental requirements for private and secure personal information and should be implemented and consistently used. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence, different privacy practices should be maintained for different personal data types in each country.

Despite the foregoing, the present disclosure also contemplates examples in which users control (e.g., selectively block or restrict access to) use of the personal information data. That is, the present disclosure contemplates that hardware and/or software elements can be provided to provide the user(s) with this control. For example, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the appl. The user may also select which information (e.g., email address) to withhold.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health-related applications, data de-identification can be used to protect a user's privacy. De-identification may be facilitated, when appropriate, by removing specific identifies (e.g., date of birth, etc.), controlling the amount or specificity of data stored (e.g., collecting location data at city level, rather than at an address level), controlling how data is stored (e.g., aggregating data across users), and/or other methods.

Therefore, although the present disclosure broadly covers use of personal information data to implement one or more various disclosed examples, the present disclosure also contemplates that the various examples can be implemented without the need for accessing such personal information data. That is, the various embodiments of the present technology are not rendered inoperable due to the lack of all or a portion of such personal information. For example, content can be selected and delivered to users by inferring preferences based on non-personal information data or a bare minimum amount of personal information, such as the content being requested by the device associated with a user, other non-personal information available, or publicly available information.

A method for measuring physiological information is disclosed. The method can comprise: detecting and measuring motion using one or more sensors, where the measured motion is associated with motion information; determining whether the motion information meets one or more continuous motion criteria; determining whether the motion is associated with one or more predetermined activities; and in accordance with the motion information meeting the one or more continuous motion criteria and the motion being associated with the one or more predetermined activities, measuring the physiological information using one or more light detectors. Additionally or alternatively, in some examples, the method further comprises: incrementing a counter until the motion is detected and measured; and delaying the measurement of the physiological information until the counter has reached an inter-sampling waiting time threshold. Additionally or alternatively, in some examples, the method further comprises: waiting a predetermined amount of time after detecting the motion, wherein signals from the one or more sensors are excluded during the predetermined amount of time. Additionally or alternatively, in some examples, the method further comprises: determining whether the measurement of the physiological information meets physiological criteria; in accordance with the measurement being successful, waiting a first amount of time; in accordance with the measurement not being successful, waiting a second amount of time, wherein the second amount of time is less than the first amount of time; and delaying a subsequent motion measurement by the respective amount of time. Additionally or alternatively, in some examples, the method further comprises: determining whether the measurement of the physiological information was successful; and in accordance with the measurement not being successful, adjusting operating conditions of the one or more light detectors. Additionally or alternatively, in some examples, determining whether the measurement of the physiological information was successful includes: determining whether a confidence value meets a confidence value threshold. Additionally or alternatively, in some examples, the method further comprises: determining whether the measurement of the physiological information was successful; in accordance with the measurement being successful: determining a time duration until the measurement was successful; adjusting a waiting period based on the time duration; and delaying a subsequent motion measurement by the adjusted waiting period. Additionally or alternatively, in some examples, wherein determining whether the motion information meets one or more continuous motion criteria includes: determining whether the motion information is within a range of motion signal values for a continuous motion time period. Additionally or alternatively, in some examples, the one or more sensors include at least one accelerometer, and wherein determining whether the motion is associated with one or more predetermined activities includes: determining whether an acceleration signal from the at least one accelerometer matches one or more patterns; and determining whether a step count is within a range of step count values. Additionally or alternatively, in some examples, the method further comprises: in accordance with the determination that the motion is associated with the one or more predetermined activities, operating the one or more light detectors in a predetermined activity mode. Additionally or alternatively, in some examples, the method further comprises: adding an amount of time spent for the measurement of the physiological information to a time counter; determining whether the time counter meets a time threshold; and in accordance with the determination that the time counter meets the time threshold, delaying subsequent measurements until a time budget has been reached. Additionally or alternatively, in some examples, the one or more sensors are included in a device, the method further comprising: determining a battery life of the device; and dynamically switching from measuring the physiological information using first operating conditions to second operation conditions, different from the first operating conditions, when the battery life is less than a battery life threshold. Additionally or alternatively, in some examples, the method further comprises: operating the one or more sensors and the one or more light detectors in a first mode; and in accordance with the motion information meeting the one or more continuous motion criteria and the motion being associated with the one or more predetermined activities, operating the one or more sensors and the one or more light detectors in a second mode, different from the first mode.

A device is disclosed. The device can comprise: one or more sensors configured to detect and measure motion and output one or more signals indicative of the measured motion; one or more light sources configured to emit light, wherein the one or more light sources are included in a plurality of optical components; one or more light detectors configured to detect a reflection of the emitted light, wherein the one or more light detectors are included in the plurality of optical components; and logic configured to: while the plurality of optical components is operating in a sleep state: determine whether the measured motion meets one or more continuous motion criteria, determine whether the measured motion is associated with one or more predetermined activities; and in accordance with the measured motion meeting the one or more continuous motion criteria and the measured motion being associated with the one or more predetermined activities: operating the plurality of optical components in a predetermined activity mode, emitting the light with the one or more light sources, detecting the reflection of the emitted light with the one or more light detectors, and determining physiological information based on the reflection of the emitted light. Additionally or alternatively, in some examples, the one or more sensors include an accelerometer and the one or more motion signals are acceleration signals. Additionally or alternatively, in some examples, the method further comprises: determining whether the motion is associated with one or more predetermined activities includes: determining whether an acceleration signal value of at least one of the acceleration signals is within a predetermined range of acceleration signal values; and determining whether a step count is within a range of step count values. Additionally or alternatively, in some examples, the device further comprises: a counter, wherein a value of the counter is continually incremented until the value of the counter meets an inter-sampling wait time threshold, wherein the switching the mode of one or more light sources and the one or more light detectors to a predetermined activity mode is delayed until the value of the counter meets the inter-sampling wait time threshold. Additionally or alternatively, in some examples, the one or more predetermined activities include walking. Additionally or alternatively, in some examples, the device further comprises: a battery configured to supply power to the device, wherein the battery has a battery life, wherein the plurality of optical components are configured to operate with first operating conditions when the battery life is greater than or equal to a battery life threshold and configured to operate with second operating conditions, different from the first operating conditions, when the battery life is less than the battery life threshold.

A method for operating a device is disclosed. The method can comprise: while a plurality of optical components is operating in a sleep state, wherein the plurality of optical components includes one or more light sources and one or more light detectors: operating one or more sensors included in the device; measuring motion of the device using the one or more sensors, where the measured motion is associated with motion information; determining whether the motion information meets one or more continuous motion criteria; determining whether the motion is associated with one or more predetermined activities; and in accordance with the motion information meeting the one or more continuous motion criteria and the motion being associated with the one or more predetermined activities: operating the plurality of optical components in a predetermined activity mode; emitting light with the one or more light sources; detecting a reflection of the emitted light with the one or more light detectors; and measuring the physiological information using the one or more light detectors. Additionally or alternatively, in some examples, determining whether the motion information meets one or more continuous motion criteria includes: determining whether the motion information is within a range of motion signal values for a continuous motion time period. Additionally or alternatively, in some examples, the one or more sensors includes at least one accelerometer configured to output an acceleration signal, and where determining whether the motion is associated with one or more predetermined activities includes: determining whether an acceleration signal value of the acceleration signal is within a predetermined range of acceleration signal values; and determining whether a step count is within a range of step count values.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:
1. A device comprising:
one or more sensors configured to measure motion and output one or more motion signals indicative of the measured motion;

one or more light sources configured to emit light;
one or more light detectors configured to detect a reflection of the emitted light; and
a processor configured to:
- determine that the measured motion matches a motion criteria in response to determining that the measured motion changed from a first defined range to a second defined range;
- in accordance with the measured motion continuing to satisfy the motion criteria for a time threshold, determine whether the one or more motion signals are associated with a predetermined activity; and
- in accordance with determining that the one or more motion signals are associated with the predetermined activity:
  - emit the light with the one or more light sources;
  - detect the reflection of the emitted light with the one or more light detectors; and
  - determine physiological information based on the reflection of the emitted light.

2. The device of claim 1, wherein:
the one or more sensors comprise an accelerometer; and
the one or more motion signals comprise acceleration measurements.

3. The device of claim 2, wherein:
the first defined range comprises acceleration values associated with a first activity; and
the second defined range comprises acceleration values associated with a second activity.

4. The device of claim 3, wherein:
the first activity comprises sitting; and
the second activity comprises one of walking, running, biking, or climbing stairs.

5. The device of claim 2, wherein determining that the measured motion matches the motion criteria comprises determining that the measured motion remains within the second defined range.

6. The device of claim 2, wherein the processor is configured to:
in accordance with the measured motion continuing not satisfying the motion criteria for the time threshold, the processor is configured to:
stop measuring the motion;
wait an amount of time; and
in response to waiting the amount of time:
  increment an inter-sampling timing counter; and
  continue to measure the motion and output the one or more motion signals indicative of the measured motion.

7. The device of claim 6, wherein the amount of time is based on a current value associated with the inter-sampling timing counter.

8. The device of claim 6, wherein the amount of time is based on at least one of a battery life of the device, a sampling frequency of the one or more sensors, or a computational load of the device.

9. A method of operating a physiological measurement device, the method comprising:
measuring motion of a user using a motion sensor at the physiological measurement device;
outputting one or more signals indicative of the measured motion;
determining that the measured motion matches a motion criteria in response to determining that the one or more signals change from a first defined range to a second defined range;
in accordance with the measured motion continuing to satisfy the motion criteria for a time threshold, determining whether the one or more signals are associated with a predetermined activity; and
in accordance with determining that the one or more signals are associated with the predetermined activity:
  emitting light with one or more light sources;
  detecting a reflection of the emitted light with one or more light detectors; and
  determining physiological information of the user based on the reflection of the emitted light.

10. The method of claim 9, wherein:
the motion sensor comprises an accelerometer configured to output an acceleration signal: and
determining that the measured motion matches the motion criteria comprises determining whether an acceleration signal value of the acceleration signal is within a defined range of acceleration signal values.

11. The method of claim 9, wherein:
the motion sensor comprises an infrared sensor configured to output a signal: and
determining that the measured motion matches the motion criteria comprises determining whether a signal value of the signal is within a defined range of infrared signal values.

12. The method of claim 9, further comprising
prior to determining that the one or more signals are associated with the predetermined activity, emitting light having a first wavelength; and
in accordance with determining that the one or more signals are associated with the predetermined activity, emitting light having a second wavelength.

13. The method of claim 12, wherein
the first wavelength comprises an infrared wavelength; and
the second wavelength comprises a green wavelength.

14. The method of claim 9, wherein in accordance with the measured motion continuing not satisfying the motion criteria for the time threshold:
stopping measuring the motion of the user;
waiting an amount of time; and
in response to waiting the amount of time, continuing to measure the motion and output the one or more signals indicative of the measured motion.

15. The method of claim 14, wherein the amount of time is based on at least one of a battery life of an electronic device, a sampling frequency of one or more sensors, or a computational load of the electronic device.

16. A wearable electronic device comprising:
a motion sensing unit comprising one or more motion sensors and configured to:
  detect, using the one or more motion sensors, motion data corresponding to motion of the wearable electronic device;
  determine whether the motion data meets one or more motion criteria for a time threshold;
  in accordance with measured motion continuing to satisfy the one or more motion criteria for the time threshold, determine whether one or more signals are associated with a predetermined activity; and
  output a signal in response to determining that the one or more signals are associated with the predetermined activity; and
a physiological measurement unit comprising one or more light detectors and configured to initiate, using the one or more light detectors, measurement of physiological information in response to the signal.

17. The wearable electronic device of claim 16, wherein the physiological measurement unit further comprises:
   a first light source configured to emit first light having a first wavelength; and
   a second light source configured to emit second light having a second wavelength.

18. The wearable electronic device of claim 17, wherein:
   the first wavelength comprises an infrared wavelength; and
   the second wavelength comprises a green wavelength.

19. The wearable electronic device of claim 16, wherein the physiological measurement unit is further configured to:
   determine whether the measurement of the physiological information is successful; and
   in accordance with the measurement not being successful, adjust an operating condition of the one or more light detectors.

* * * * *